(12) United States Patent
Knapp et al.

(10) Patent No.: US 7,835,802 B2
(45) Date of Patent: *Nov. 16, 2010

(54) POLYMER LEAD COVERING WITH VARIED MATERIAL PROPERTIES

(75) Inventors: Christopher P. Knapp, Ham Lake, MN (US); Kyle Hoecke, Lino Lakes, MN (US); Mohan Krishnan, Shoreview, MN (US); Rebecca Aron, Ann Arbor, MI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 441 days.

This patent is subject to a terminal disclaimer.

(21) Appl. No.: 12/046,407

(22) Filed: Mar. 11, 2008

(65) Prior Publication Data

US 2008/0161871 A1    Jul. 3, 2008

Related U.S. Application Data

(63) Continuation of application No. 11/150,021, filed on Jun. 10, 2005, now Pat. No. 7,366,573.

(51) Int. Cl.
*A61N 1/02* (2006.01)
(52) U.S. Cl. ........................... 607/121; 607/116
(58) Field of Classification Search ......... 607/116–117, 607/119, 121, 152
See application file for complete search history.

(56) References Cited

U.S. PATENT DOCUMENTS

| | | | |
|---|---|---|---|
| 4,643,202 A | 2/1987 | Roche | |
| 5,090,422 A | 2/1992 | Dahl et al. | |
| 5,358,516 A | 10/1994 | Myers et al. | |
| 5,755,762 A | 5/1998 | Bush | |
| 5,931,862 A | 8/1999 | Carson | |
| 6,070,104 A | 5/2000 | Hine et al. | |
| 6,477,428 B1 | 11/2002 | Skinner et al. | |
| 6,546,292 B1 | 4/2003 | Steinhaus et al. | |
| 6,704,604 B2 | 3/2004 | Soukup et al. | |
| 6,718,211 B2 | 4/2004 | Smits | |
| 2003/0023294 A1 | 1/2003 | Krall et al. | |
| 2003/0181966 A1 | 9/2003 | Morgan | |
| 2003/0220677 A1 | 11/2003 | Doan et al. | |
| 2004/0059402 A1 | 3/2004 | Soukup et al. | |
| 2004/0249430 A1 | 12/2004 | Martinez et al. | |
| 2005/0060004 A1 | 3/2005 | Cooke et al. | |
| 2006/0282144 A1 | 12/2006 | Knapp et al. | |
| 2006/0282146 A1 | 12/2006 | Aron et al. | |

OTHER PUBLICATIONS

"U.S. Appl. No. 11/150,021, Notice of Allowance mailed Dec. 12, 2007", 4 pgs.
"U.S. Appl. No. 11/150,021 Response filed Nov. 14, 2007 to Final Office Action mailed Sep. 14, 2007", 11 Pages.
"Final Office Action Mailed Sep. 14, 2007 in U.S. Appl. No. 11/150,021", 11 pages.

*Primary Examiner*—Carl H Layno
*Assistant Examiner*—Luther G Behringer
(74) *Attorney, Agent, or Firm*—Faegre & Benson LLP (57) ABSTRACT

This document discusses, among other things, a lead assembly including a lead body, at least one conductor extending through the lead body, and a covering having varied material properties. In an example, the covering is made by forming pieces of material having varied material properties. In another example, the covering is made by varying parameters such as heat or tension during wrapping of a piece of material onto a lead assembly.

22 Claims, 6 Drawing Sheets

POLYMER LEAD COVERING WITH VARIED MATERIAL PROPERTIES

CROSS-REFERENCE TO RELATED APPLICATIONS

This application is a continuation of U.S. patent application Ser. No. 11/150,021, now U.S. Pat. No. 7,366,573, filed on Jun. 10, 2005, the specification of which is incorporated herein in its entirety by reference.

TECHNICAL FIELD

This patent document pertains generally to medical device lead assemblies, and more particularly, but not by way of limitation, to polymer lead coverings having varied material properties.

BACKGROUND

Medical devices such as pacers and defibrillators typically include at least one lead assembly. In a defibrillator, for example, a lead assembly typically includes at least one defibrillation electrode, such as a defibrillation coil. Some lead assemblies include a cover that extends over at least a portion of the outer surface of the lead assembly. A cover may extend over a defibrillation coil, for example. Covers are used, for example, to prevent tissue ingrowth. Some covers are formed from polytetrafluoroethylene (PTFE). Improved coverings for lead assemblies are needed.

SUMMARY

An example lead assembly includes a lead body for a medical device lead assembly, at least one conductor extending through the lead body, a first cover formed from a polymer and extending over a first portion of the lead body, and a second cover formed from the polymer and extending over a second portion of the lead body. The first cover has a first set of material properties. The second cover has a second set of properties. At least one of the second set of material properties is different from the first set of properties. In an example, the first cover includes a first sheath and the second cover includes a second sheath. In an example, the first sheath is joined to the second sheath. In an example, the lead assembly further includes a polymer strip helically wrapped around the lead body, the polymer strip forming the first cover and the second cover. In an example, a first portion of the polymer strip forming the first cover is wrapped at a first tension, and a second portion of the polymer strip forming the second cover is wrapped at a second tension that is different than the first tension. In another example, the ultra-high molecular weigh polyethylene lead assembly includes a polymer coating on the lead body, the coating including the first cover and the second cover. In an example, the first cover is porous and the second cover is non-porous. In an example, a lead assembly includes a drug disposed in at least some of the pores in the first cover. In an example, the polymer is polytetrafluoroethylene (PTFE) or ultra-high molecular weigh polyethylene. The polymer is optionally expanded. In an example, the second cover includes an expanded polymer and a filler disposed in pores in the second cover. In an example, the filler is silicone or polyurethane.

In another example, a lead assembly includes a lead body for a medical device lead assembly, at least one conductor extending through the lead body, at least one electrode, and a cover extending over at least a portion of the lead body. The cover is formed from a polymer. A first portion of the cover has a first set of properties, and a second portion of the cover has a second set of properties. At least one of the second set of properties different from at least one of the first set of properties. In an example, the first portion of the cover has a first dielectric strength and the second portion of the cover has a second dielectric strength that is different than the first dielectric strength.

An example method includes forming a cover of polymer having a porosity, applying the cover to a medical device lead assembly, and selectively varying the porosity of the polymer at locations on the cover. In an example, applying the cover includes wrapping a strip of polymer material on the medical device lead assembly under tension, and selectively varying the porosity of the polymer at locations on the cover includes selectively controlling the tension during wrapping of the strip of polymer material. In an example, wrapping the strip of polymer material on the medical device lead assembly includes wrapping a first portion of the cover at a first tension and wrapping a second portion at a second tension lower than the first tension, wherein wrapping the first portion at the first tension creates larger pores than wrapping the second portion at the second tension. In an example, selectively varying the porosity of the polymer at locations on the cover includes applying a filler to a first portion of the cover, the filler filling at least a portion of a multiplicity of pores in the first portion of the cover. In an example, selectively varying the porosity of the polymer at locations on the cover includes applying heat to the polymer.

Another approach includes forming a first cover formed from an expanded first polymer, forming a second cover from a nonexpanded first polymer, applying the first and second covers to a medical device lead assembly, and joining the first cover to the second cover. In an example, applying the first and second covers includes wrapping respective first and second strips of polymer material around the medical device lead assembly. In an example, the method further includes applying a third cover formed from the polymer to the medical device lead assembly, the third cover formed from an expanded polymer, and joining the third cover to the second cover.

BRIEF DESCRIPTION OF THE DRAWINGS

In the drawings, which are not necessarily drawn to scale, like numerals describe substantially similar components throughout the several views. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments are also referred to herein as "examples." The drawings and following detailed description is not to be taken in a limiting sense, and the scope of the present invention is defined by the appended claims and their equivalents.

A medical device lead assembly includes a polymer covering extending over at least a portion of the lead assembly and having varied properties at locations on the lead assembly. In an example, performance, reliability, and/or manufacturability are enhanced by varying material properties in the polymer cover. The varied properties in the polymer covering can be achieved by using two or more cover segments that are made from polymer materials having different properties (e.g. different porosities), by controlling parameters such as tension and heat during application of a polymer material to a lead assembly, and/or by varying the material properties after the polymer covering is applied to the lead assembly. Varied properties can also be produced by forming a piece of polymer having varying properties, and then applying the polymer to a lead assembly. In an example, properties are imparted to portions of the lead based upon the performance requirement of specific portions of the lead. In an example, properties of a lead are supplied so that electrical conductivity is provided near electrodes, tissue ingrowth and drug loading is supported at a fixation point such as at distal tip, and/or knick-resistance is provided where needed, such as near a terminal.

Forming a cover from a single polymer having varying material properties can provide a number of advantages. In an example, a covering having varying material properties provides desirable handling characteristics, such as flexibility, pushability, and/or abrasion resistance. Varying forms (e.g. expanded and non-expanded polytetrafluoroethylene (PTFE)) of a single polymer tend to bond well, while bonds between dissimilar materials (e.g. polyethylene and PTFE) can provide weak points in a lead assembly. In an example, varying the properties in lead assembly covering limits fibrotic adhesion and tissue ingrowth and supports extractability of a lead. In an example, a portion of a lead is laser-markable, thereby eliminating the need for a label.

Figure 1:
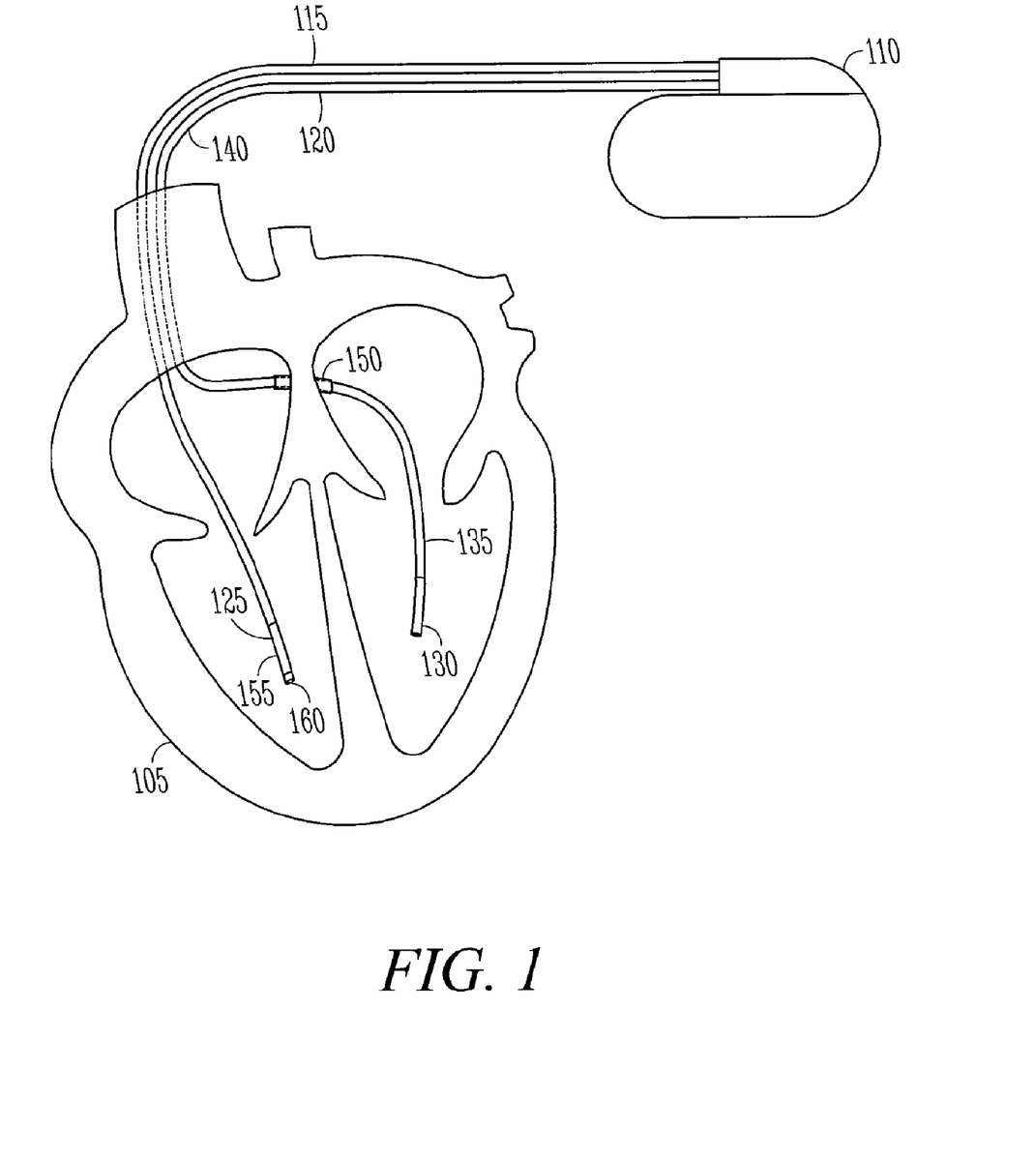
FIG. 1 shows an example system for monitoring and stimulating a heart including a lead having a covering with varied material properties.
Figure 6:
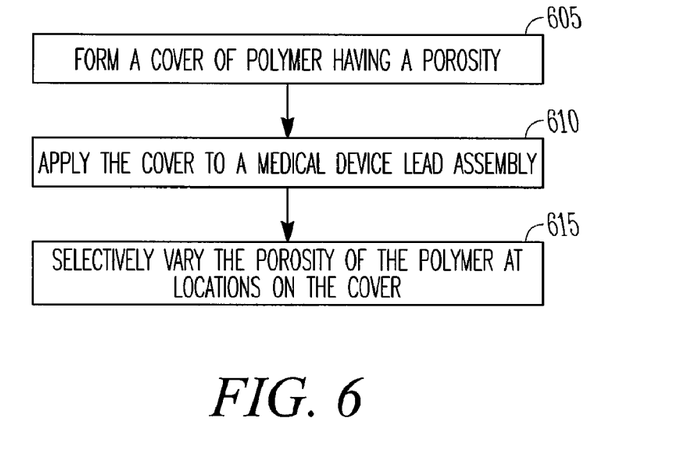
FIGS. 6 and 7 are flow charts that illustrate a method of applying polymer material to a lead assembly.
Figure 7:
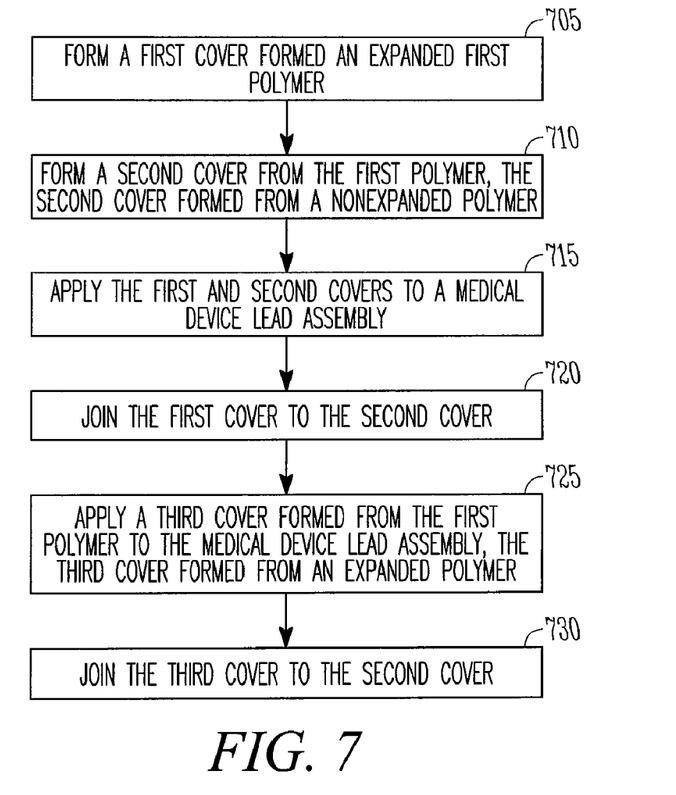

FIG. 1 shows an example system for monitoring and stimulating a heart that includes at least one lead assembly including a covering having varied material properties at locations on the lead assembly. FIGS. 2, 3A-3B, 4, 5, and 6A-6B show lead assemblies and example coverings. FIGS. 6 and 7 are flowcharts that illustrate methods of producing lead assemblies having varying material properties at locations on a covering.

Referring now to FIG. 1, an example system for monitoring and stimulating a heart 105 includes a medical device 110 and at least one lead assembly including at least one covering having varied material properties at varied locations on the covering. In an example, the lead assembly is a pacing lead, defibrillation lead, or neurological lead. In an example, the lead assembly delivers an antitachyarrhythmia therapy, bradycardia therapy, heart failure therapy, or neural stimulation, for example. In an example, the medical device 110 is a pacer, defibrillator, or stimulator.

In an example, two or more lead assemblies are coupled to the medical device. In FIG. 1, one lead assembly 115 extends into the right side of the heart. The other lead assembly 120 extends into the left side of the heart. In another example, the medical device 110 is coupled to a single lead assembly that extends, for example, into either the right or left side of the heart. In other examples, a lead assembly extends on or around the heart, or on or around a nerve truck or other anatomical target.

Referring again to FIG. 1, each lead assembly includes at least one covering 125, 130 having varied material properties at varied locations on the lead assembly. In an example, a covering includes two or more covers, such as sheaths, that have different material properties. In an example, the covers are formed from the same polymer, but have different material properties, such as different stiffnesses or porosities. In an example, the two covers are joined together. In an example, a portion 135 of a cover 130 that is inserted through the coronary sinus 150 during implant is more flexible than a portion 140 of the cover 130 that is not inserted through the coronary sinus. In another example, a portion 155 of a cover near a distal end 160 of a lead assembly includes pores sized to support tissue ingrowth, and other portions of the cover are not porous or includes pores sized to inhibit tissue ingrowth.

Figure 2A:
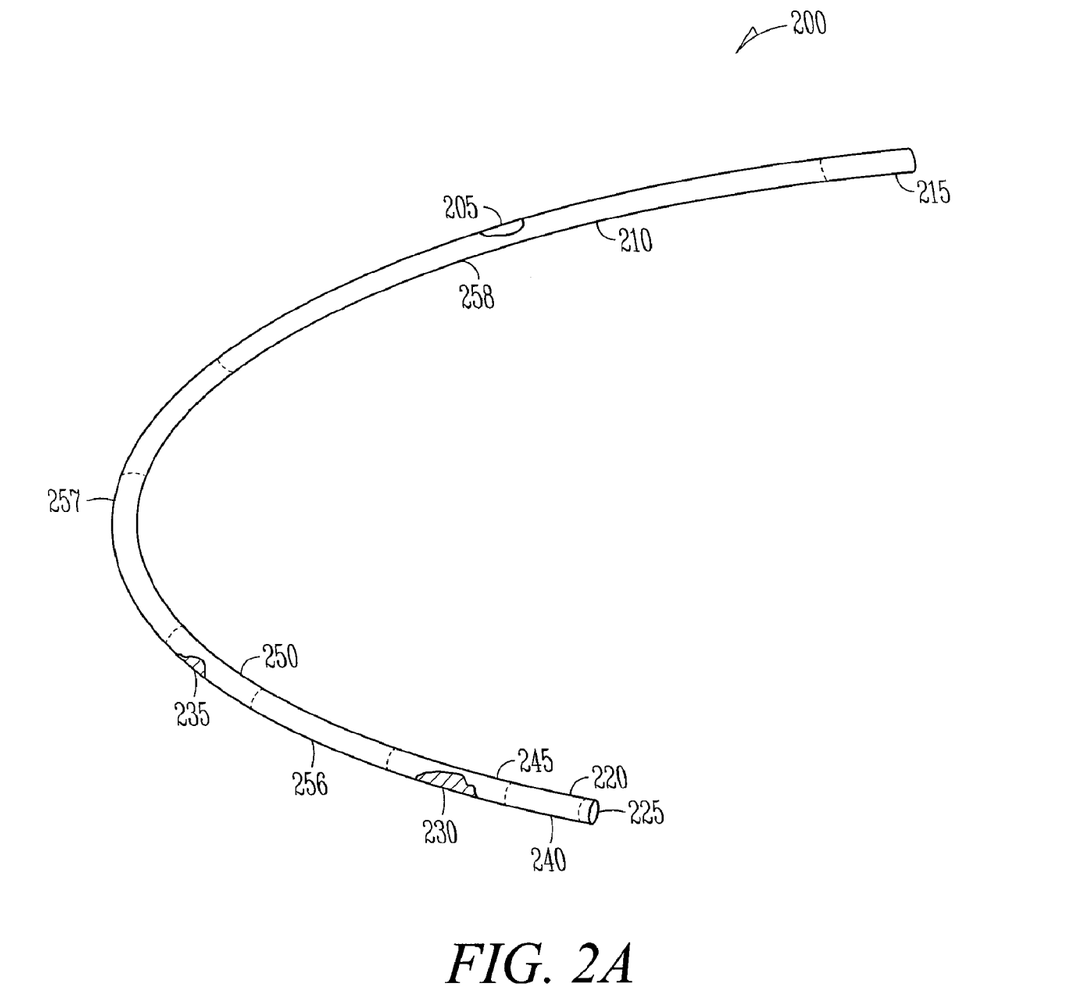
FIG. 2A shows a medical device lead assembly that includes a cover having varied material properties.

FIG. 2A shows another example medical device lead assembly 200. The lead assembly 200 includes one or more conductors extending through a lumen in a lead body 205, and a covering 210 extending over the lead body. In an example, the lead body 205 is made of silicone. In an example, the lead body 205 is a tube that includes at least one lumen. The covering 210 has varied material properties at locations on the lead assembly. A proximal end 215 of the lead assembly 205 is connectable to a medical device. A distal end 220 of the lead assembly is implantable in, on, or around a heart. The conductors in the lead assembly are electrically coupled to one or more electrodes. In an example, the lead assembly includes a first defibrillation electrode 230, a second defibrillation electrode 235, and a sensing/pacing electrode 225. The covering is shown partially cut-away in FIG. 2A to show the defibrillation electrodes 230, 235 beneath the covering.

Referring again to FIG. 2A, for the purpose of illustration, example locations of the covering having particular material properties are indicated with a dotted line in FIG. 2A. In an example, a first location on the covering has a first set of properties including porosity, dielectric strength, knick-resistance, strength, and/or lubricity, for example, and a second location on the covering has a second set of properties, at least one of which is quantifiably different from the first set. In an example, at a location 240 near the distal end 220 of the lead, the covering 210 has a porosity that allows tissue ingrowth to fixate the distal end of the lead. At locations 245, 250 near the defibrillation electrodes 230, 235, the covering 210 has a porosity that supports conduction of electricity through the cover. In an example, an antitachyarrhythmia therapy is effectively delivered through a cover having a porosity that supports electrical conduction. In an example, the pores in the cover at locations near the defibrillation electrodes are large enough to support conductivity, but small enough to prevent tissue ingrowth. In an example, at a location 256 on the covering 210 that extends through particularly complex vasculature when implanted, the cover has an increased flexibility. In an example, other portions of the cover 257, 258 have enhanced knick-resistance and/or abrasion resistance to improve the durability of the cover. In an example, the covering 210 is formed by wrapping a piece of polymer material onto the lead assembly, and the material property variations are pre-manufactured into the piece of material or are created as the polymer material is wrapped onto the lead assembly.

In an example, the lead assembly covering is formed from polytetrafluoroethylene (PTFE) and expanded polytetrafluoroethylene (ePTFE). In an example, the ends of a lead assembly include ePTFE that allows tissue ingrowth to fixate the ends of the lead, and other portions of the lead include less porous or fully dense PTFE. Fully dense PTFE provides good abrasion resistance, dielectric integrity, and lubricity. In an example, portions of a covering near or over an electrode, such as a defibrillation electrode, are formed from ePTFE to provide electrical conductivity through the covering, and portions near a terminal are formed from fully dense PTFE to provide knick-resistance.

In other examples, a covering is formed from polyethylene (PE), polypropylene (PP), fluorinated ethylene propylene (FEP), ethylene-tetrafluoroethylene (ETFE), or another biocompatible polymer. In an example, at least part of a cover includes expanded polymer. Expanded polymers bond well with a non-expanded version of the same polymer, but have different material properties.

Figure 2B:
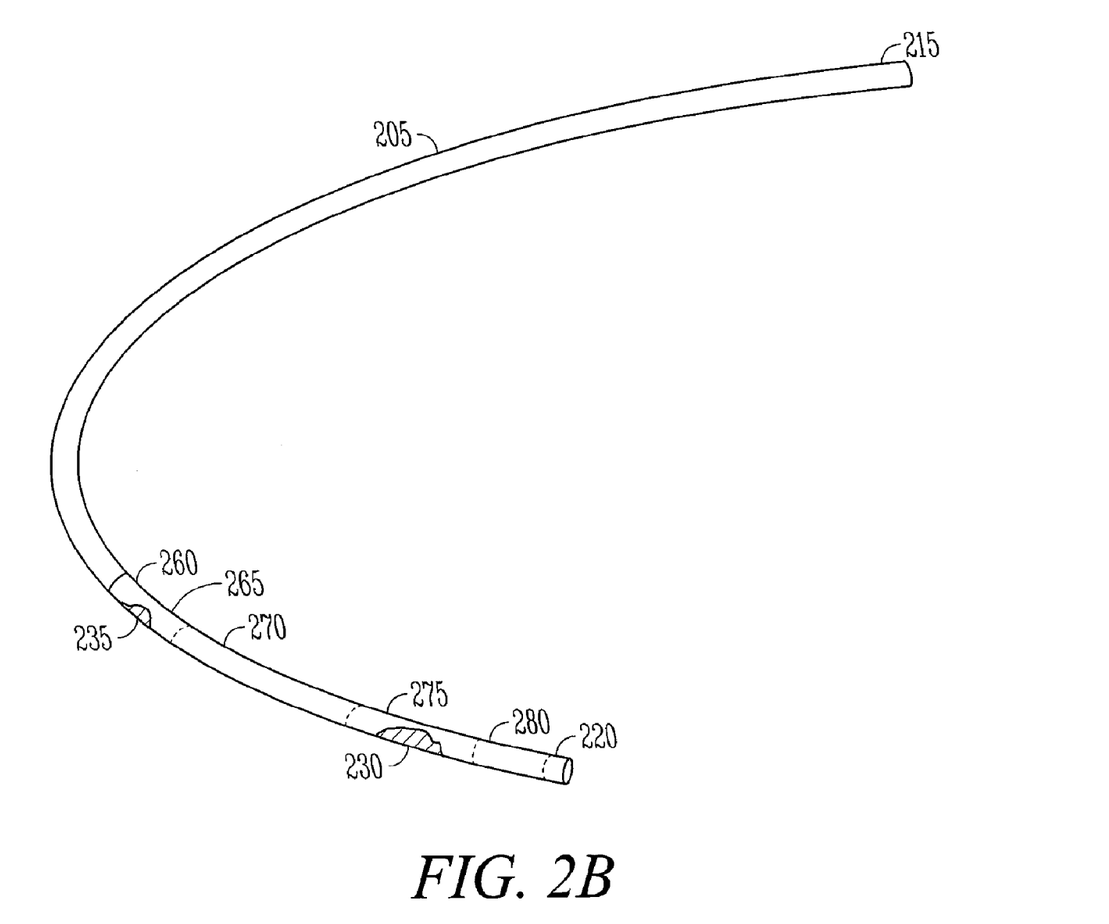
FIG. 2B shows a medical device lead assembly that includes a cover extending having varied material properties extending over a portion of a lead.

Referring now to FIG. 2B, in another example, a covering 260 includes separate covers 265, 270, 275 having different material properties. In an example, the covers 265, 270, 275 are made from different forms (e.g. varying porosity) of the same polymer. In an example, the covers 265, 270, 275 are joined together, for example by heat bonding, adhesive bonding, welding, solvent bonding, or laser sintering. Covers 265, 275 extend over defibrillation electrodes 230, 235 and a portion of a lead body 205. In an example, at least a portion of the covers 265, 275 extending over the electrodes 230, 235 are conductive. In an example, the covers 265, 275 have pores that fill with body fluid, which conducts electricity. Cover 270 extends between the other two covers 265, 275. In an example, cover 270 is not porous, and has good abrasion resistance. In an example, another cover 280 near the distal end 220 has pores sized to allow tissue ingrowth.

In an example, a cover is formed by extruding a polymer into a tube or other lead body shape. In another example, a cover is formed by coating some or all of a lead assembly with a polymer, for example by spray coating or dip coating a lead assembly.

Figure 3A:
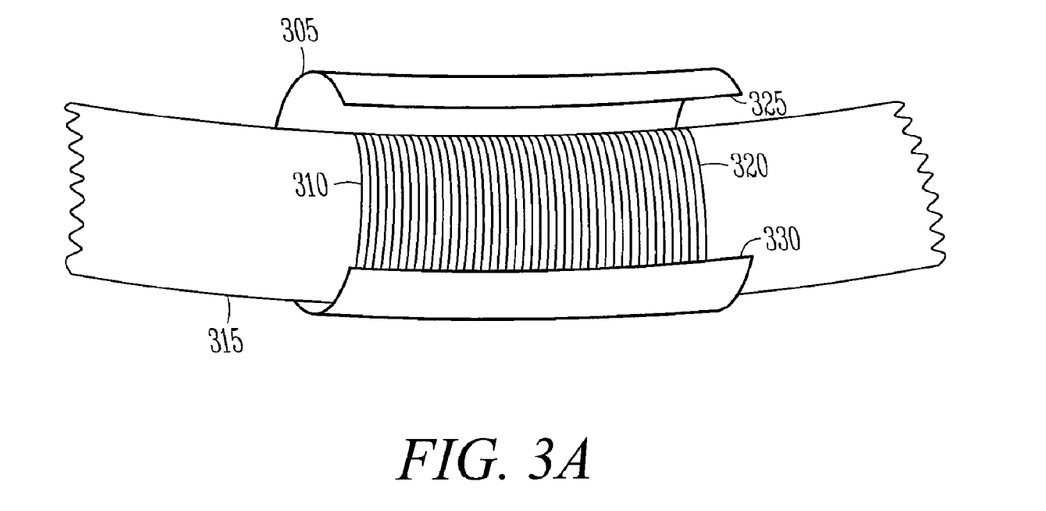
FIGS. 3A and 3B show a piece of polymer material wrapped around a portion of a medical device lead assembly to form a cover.
Figure 3B:
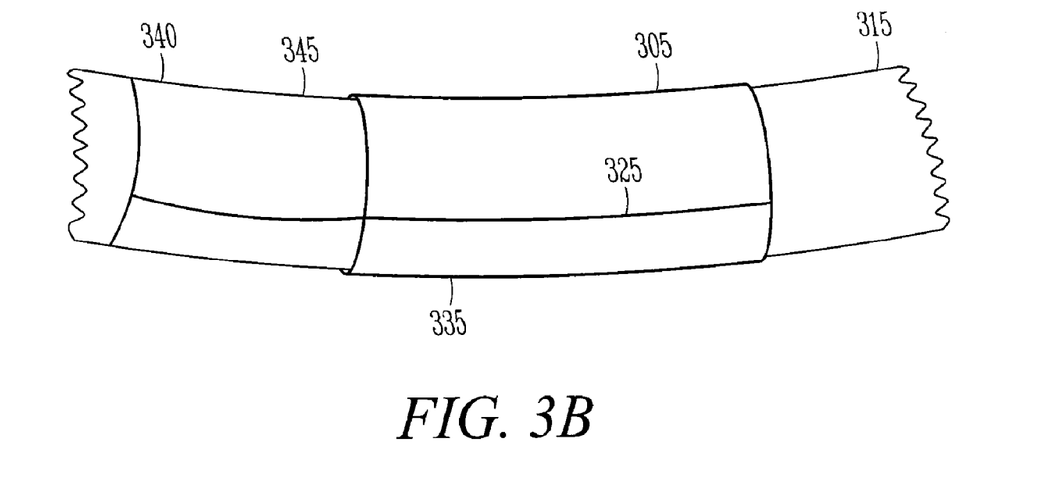

In another example, a cover is made by wrapping a piece of polymer material (e.g. polymer tape) around a lead assembly, as illustrated by FIGS. 3A and 3B. A piece of polymer material 305 is wrapped around at least a portion of a lead assembly 315. The piece includes a first edge 325 and a second edge 330. The first edge 325 meets or overlaps with the second edge 330, as shown in FIG. 3B. In an example, the piece of polymer material 305 is wrapped around an electrode 310 that includes, for example a wire 320 wrapped into a coil. In an example, the material 305 forms a generally tubular cover 335. In an example, the polymer material 305 extends beyond the electrode. In an example, the material 305 covers most or all of the lead assembly.

The polymer material 305 is secured on the lead assembly, for example, by joining the cover to itself. In an example, at least a portion of the polymer material 305 is heated to fuse the polymer material to itself. In an example, the polymer material 305 is sintered proximate the first edge 325. In an example, the polymer cover 335 is sintered with a laser, infrared (IR) wand, heat gun, or oven. In an example, the heating of the material also conforms the polymer material to the outer shape of the electrode or lead body. In an example, the material properties in a portion of the cover are modified by heating the portion of the cover.

In an example, a second piece of polymer material 340 is wrapped on the lead 315 to form a second cover 345 adjacent to the first cover 335. In an example, the second cover 345 is formed from the same material as the first cover 335, and optionally has different material properties. In an example, the first and second pieces 305, 340 are wrapped with different tensions, and/or at different temperatures, to impart different material properties to the polymer. In an example, the second cover 345 is joined to the first cover 335, for example by laser sintering. In an example, the pieces of polymer material 305, 340 include pores at the edges, in which an adhesive is disposed. The adhesive supports bonding of the pieces of material to each other or to themselves at locations of material overlap.

Figure 4:
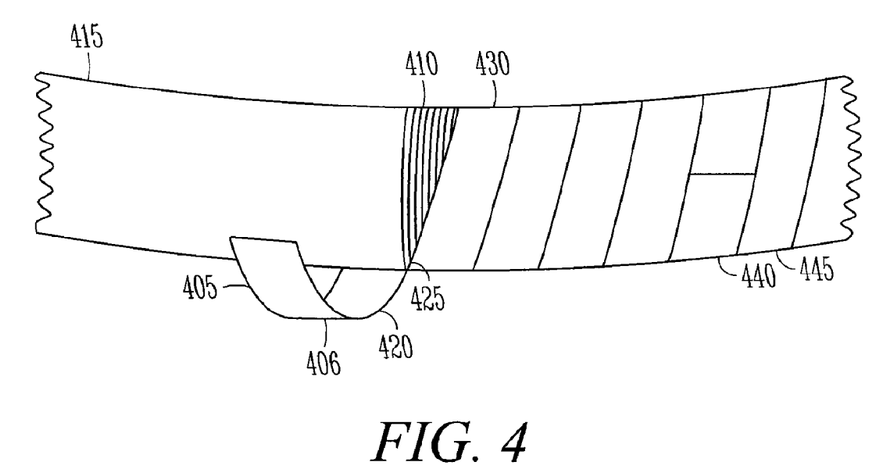
FIG. 4 shows a piece of polymer material wrapped spirally around a portion of a medical device lead assembly to form a cover.

Referring now to FIG. 4, another method of applying a polymer material to a lead assembly is shown. A strip 405 of polymer material 406 is wrapped in a spiral around at least a portion lead assembly 415. In an example, a first edge 420 of the strip 405 meets or overlaps with a second edge 425 of the piece from a previous wrap around the lead assembly. The spiral-wrapped piece of polyethylene forms a cover 430.

In an example, a second piece 440 of polymer material is wrapped around the lead assembly to form a second cover 445 adjacent to the first cover. In an example, the first cover 430 extends over the electrode 410 and has a porosity that supports conductivity through the cover, and the second cover has no pores, or a lower porosity than the first cover, to provide desired durability. In an example, the second cover 445 is joined to the first cover 430, for example by laser sintering. In an example, the second cover is formed from the same material as the first cover, and the second cover has material properties that are different than the first cover. In an example, the first cover is formed from ePTFE and the second cover is formed from PTFE.

In an example, the material properties vary within the cover 410. In an example, some or all of the cover 410 is porous. In an example, all of the lead assembly is covered except a fixation mechanism at or near the distal tip, and a terminal that connects to a medical device. In an example, the strip of material is manufacture with regions of that have varying material properties before application to the lead assembly. When the strip material is wrapped on the lead assembly, the cover has regions having varied properties determined at least in part by the variations that are manufactured into the raw polymer material. In an example, the location on the lead assembly of regions having particular properties can be calculated using the diameter of the lead body, the width of the strip, and the stretching characteristics of the polymer.

In another example, the material properties are varied in the cover 430 by controlling parameters such as heat and tension in the polymer during the wrapping process. In another example, the material properties of the cover are modified after the cover is applied, for example by heating a portion of the cover. In some examples, a combination of these four techniques (separate covers, pre-manufactured variations in the strip, controlling application parameters, and post-application processing) is used to achieve a cover having the desired properties.

Figure 5:
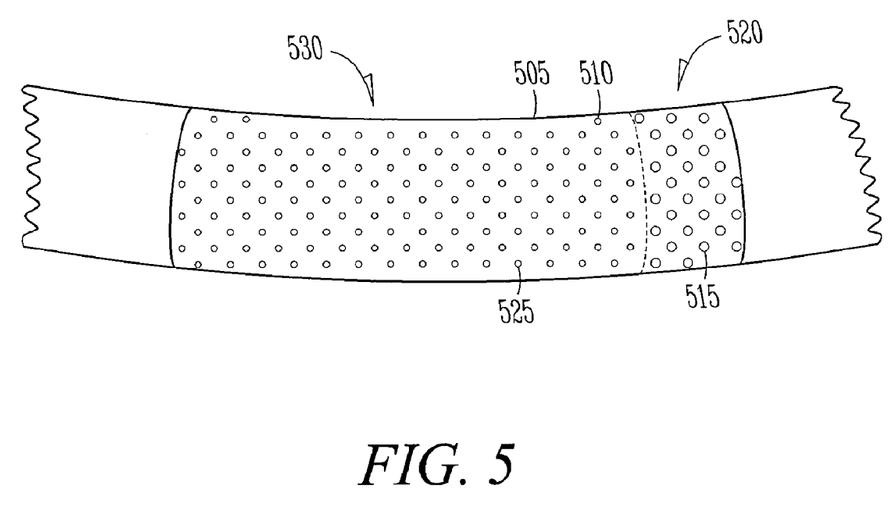
FIG. 5 shows a porous cover having pores of different sizes in different regions of the cover.

Referring now to FIG. 5, an example polymer covering 505 includes pores 510. The size of the pores is exaggerated for the purpose of illustration. In an example, the pore size in the polymer covering is controlled to control tissue ingrowth into the covering. In an example, the pores 515 in a first portion 520 of the polymer covering 505 are larger than the pores 525 in a second portion 530 of the polymer covering. For the purpose of illustration, a dotted line is provided FIG. 5 to distinguish the first portion 520 of the covering from the second portion 530. In an example, the pores 515 in the first portion 520 are large enough to allow at least some tissue ingrowth, and the pores 525 in the second portion 530 are small enough to substantially inhibit tissue ingrowth. In an example, pores are provided in the first portion to support conductivity, and other portion(s) of the covering include no pores to electrical insulate a portion of the lead. In an example, the tissue ingrowth into the pores 515 in the first portion 520 secures the lead to body tissue. In an example, the covering 505 is formed around the lead assembly using the technique illustrated in FIGS. 3A-3B or the technique illustrated in FIG. 4. In an example, the covering 505 includes two adjacent covers fused together. In another example, the covering 505 includes a single cover having material properties that vary at locations in the cover.

The size of pores in the polymer material can be controlled using one or more of a variety of techniques. In an example, a piece of polymer material is manufactured to have differing pore sizes by controlling parameters such as tension or heat during the manufacturing process. In an example, the first portion 520 and second portion 530 of the covering 505 of FIG. 5 are formed from separate pieces of polymer material.

In another example, pore size is controlled by adjusting tension applied to the polymer material as the material is assembled onto the lead assembly. In an example, a polymer cover is made using a spiral winding technique, as illustrated in FIG. 4, and the pore size is controlled by varying the tension on the piece of material 405. In another example, pore size is varied through application of heat during or after the application of the polymer material to the electrode. In an example, heating the polymer melts the polymer and/or shrinks the size of the pores. In another example, a filler is applied to porous polymer to fill in pores and change the porosity of the polymer material at a location on a cover. In an example, the polymer is ePTFE or polyethylene. In an example, the filler is silicone or polyurethane. In an example, the filler is treated to provide better adhesion to such polymers. In an example, the filler is applied to a covering in solution using spraying or dipping techniques. In an example, two or more of the preceding techniques are used concurrently or sequentially to control the pore size at one or more locations in the polymer material.

In an example, when the pores are filled with a conductive substance, such as body fluid, the pores in the polymer provide a conductive pathway for a defibrillation current. In another example, the polymer includes particles of conductive matter to make the covering itself conductive. In another example, a conductive material is deposited on the polymer to provide a conductive pathway for a defibrillation current.

In an example, a polymer cover is hydrophilicly treated. In an example, a drug is disposed in at least some of the pores of the first cover. In an example, a drug is disposed in pores in a portion of a cover near a distal end of the lead assembly.

FIG. 6 is a flow chart that illustrates a method. At 605, a cover is formed having a porosity. At 610, the cover is applied to a medical device lead assembly. In an example, the cover is formed using one of the techniques shown in FIGS. 3 and 4. In another example, the cover is formed by extrusion. At 615, the porosity of the polymer is varied at locations on the cover. In an example, the porosity is varied by varying the porosity in the polymer before it is applied to the lead assembly. In another example, the porosity is varied as the polymer is applied to the lead assembly, for example by controlling application of heat and/or tension during the application of the polymer to the lead assembly. In another example, the porosity is varied after the polymer is applied to the lead assembly, for example by filling pores at locations on the lead.

FIG. 7 illustrates another method. At 705, a first cover is formed from a polymer. In an example, the cover is formed from an expanded polymer. At 710, a second cover is formed from the same polymer. In an example, the second cover is formed from a non-expanded form of the polymer. In an example, the second cover is formed from ePTFE and the first cover is formed from ePTFE. At 715, the first and second covers are applied to a medical device lead assembly. In an example, the covers are formed in a flat form (e.g. a strip of material), and are then wound onto the medical device lead assembly, for example as shown in FIG. 3 or 4. In another example, the covers are extruded into a tube or other shape and then assembled onto a medical device lead assembly. At 720, the first cover is joined to the second cover, for example by laser sintering or adhesive bonding. At 725, a third cover is applied to the lead assembly. The third cover is formed from the expanded polymer. At 730, the third cover is joined to the second cover. In an example, the first and third covers extend over first and second defibrillation electrodes. In another example, the first cover is located at or near distal tip and includes pores sized to support tissue ingrowth.

Polymer lead coverings are also described in copending application Ser. No. 11/150,549 to Aron et al., entitled Lead Assembly with Porous Polyethylene Cover, which is incorporated by reference in its entirety.

It is to be understood that the above description is intended to be illustrative, and not restrictive. Since many embodiments of the invention can be made without departing from the scope of the invention, the invention resides in the claims hereinafter appended.

What is claimed is:

1. A lead assembly comprising:
   a longitudinally extending lead body;
   at least one conductor extending through the lead body;
   a first cover including a first polymer material and substantially extending over a first longitudinal portion of the lead body, the first cover having a first set of material properties;
   a second cover including the first polymer material and substantially extending over a second longitudinal portion of the lead body different than the first longitudinal portion, the second cover having a second set of material properties, at least one of which is different than the first set of material properties; and
   a bonding zone disposed between adjacent end portions of the first cover and the second cover, the bonding zone including a joining of the first and second covers.

2. The lead assembly of claim 1, wherein the first cover includes a first sheath and the second cover includes a second sheath.

3. The lead assembly of claim 1, wherein the first polymer material includes polytetrafluoroethylene (PTFE).

4. The lead assembly of claim 3, wherein the first cover includes expanded polytetrafluoroethylene (ePTFE).

5. The lead assembly of claim 3, wherein the second cover includes expanded polytetrafluoroethylene (ePTFE) and a filler disposed in the pores of the ePTFE.

6. The lead assembly of claim 5, wherein the filler includes at least one of silicone or polyurethane.

7. The lead assembly of claim 1, wherein at least one of the first cover or the second cover includes one or more removed hole portions.

8. The lead assembly of claim 1, wherein the first cover is porous and the second cover is non-porous.

9. The lead assembly of claim 8, wherein the first cover is disposed around a distal end portion of the lead body.

10. The lead assembly of claim 1, wherein the second cover has a greater stiffness than the first cover.

11. The lead assembly of claim 1, wherein the first cover and the second cover are joined together using at least one of heat bonding, solvent bonding, or an adhesive.

12. The lead assembly of claim 1, wherein the bonding zone hermetically seals a discontinuity between the first cover and the second cover.

13. The lead assembly of claim 1, wherein an outer surface portion of the first cover and an outer surface portion of the second cover are substantially isodiametric.

14. The lead assembly of claim 1, wherein a thickness of at least one of the first cover or the second cover varies along a length of the longitudinally extending lead body.

15. A method comprising:
forming a first cover using a first polymer material, the first cover having a first set of properties;
forming a second cover using the first polymer material, the second cover having a second set of properties;
varying the properties of at least one of the first cover or the second cover, including differing at least one property of the first set of properties from at least one property of the second set of properties;
applying the first and second covers to different longitudinal portions of a lead body; and
joining an end portion of the first cover to an end portion of the second cover.

16. The method of claim 15, wherein forming the second cover using the first polymer material includes forming the second cover from polytetrafluoroethylene (PTFE).

17. The method of claim 15, wherein forming the first cover using the first polymer material includes forming the first cover from expanded polytetrafluoroethylene (ePTFE).

18. The method of claim 17, further comprising filling pores of the first cover using at least one of a dipping or a coating process.

19. The method of claim 15, wherein varying the properties of the first cover or the second cover includes forming one or more holes in at least one of the first or second covers.

20. The method of claim 19, wherein forming the one or more holes in at least one of the first or second covers includes molding or laser cutting the holes.

21. The method of claim 15, wherein varying the properties of the first cover or the second cover includes varying a thickness of at least one of the first or second covers.

22. The method of claim 15, wherein joining the end portion of the first cover to the end portion of the second cover includes fusing the end portion of the first cover to an adjacent end portion of the second cover.

* * * * *